US012225849B2

(12) United States Patent
Walker et al.

(10) Patent No.: US 12,225,849 B2
(45) Date of Patent: Feb. 18, 2025

(54) ACTIVE LOSS MONITOR FOR A HARVESTER

(71) Applicant: CNH Industrial America LLC, New Holland, PA (US)

(72) Inventors: Eric L. Walker, Narvon, PA (US); Matthew D'Amicantonio, New Holland, PA (US); Ericson Santos, Curitiba (BR)

(73) Assignee: CNH Industrial America LLC, Holland, PA (US)

(*) Notice: Subject to any disclaimer, the term of this patent is extended or adjusted under 35 U.S.C. 154(b) by 792 days.

(21) Appl. No.: 17/466,222

(22) Filed: Sep. 3, 2021

(65) Prior Publication Data
US 2023/0072664 A1    Mar. 9, 2023

(51) Int. Cl.
*A01D 41/127*    (2006.01)
*A01D 41/12*    (2006.01)
(Continued)

(52) U.S. Cl.
CPC ..... *A01D 41/1273* (2013.01); *A01D 41/1243* (2013.01); *A01F 7/06* (2013.01);
(Continued)

(58) Field of Classification Search
CPC .... G01N 33/025; G01N 22/00; G01N 15/147; G01N 15/1459; G01N 15/1433;
(Continued)

(56) References Cited

U.S. PATENT DOCUMENTS 3,606,745 A * 9/1971 Girodat ............... A01D 41/1273
                                                460/7
3,939,846 A * 2/1976 Drozhzhin ........... A01D 41/127
                                                56/DIG. 15
(Continued)

FOREIGN PATENT DOCUMENTS

DE    102015205310 A1 * 9/2016 ......... A01D 41/1272
EP    0339140 B1    9/1993
(Continued)

OTHER PUBLICATIONS

Extended European Search Report for EP Application No. 22193779.0 dated Jan. 2, 2023 (11 pages).

*Primary Examiner* — Arpad Fabian-Kovacs
(74) *Attorney, Agent, or Firm* — Peter K. Zacharias; Rebecca L. Henkel; Rickard K. DeMille

(57) ABSTRACT

A combine has a grain sample sensor for detecting frequencies of impacts of separated grain on the grain sample sensor, a grain loss sensor for detecting frequencies of impacts of residue and lost grain on the grain loss sensor, and a controller. The controller is configured to receive, from the grain sample sensor, the frequencies of the impacts of the separated grain, receive, from the grain loss sensor, the frequencies of the impacts of the residue and the lost grain, set a detection frequency band based on the frequencies of the impacts of the separated grain, filter the frequencies of the impacts of the residue and the lost grain based on the detection frequency band, determine, from the filtered frequencies, grain loss information, and indicate the grain loss information to an operator of the combine, or control the combine based on the grain loss information.

20 Claims, 8 Drawing Sheets

(51) Int. Cl.
*A01F 7/06* (2006.01)
*A01F 12/18* (2006.01)
*G01N 15/14* (2006.01)
*G01N 33/02* (2006.01)
*G01N 15/1031* (2024.01)
*G01N 15/1433* (2024.01)
*G01N 22/00* (2006.01)

(52) U.S. Cl.
CPC ....... *A01F 12/181* (2013.01); *G01N 15/1459* (2013.01); *G01N 15/147* (2013.01); *G01N 33/025* (2013.01); *G01N 15/1031* (2013.01); *G01N 15/1433* (2024.01); *G01N 22/00* (2013.01)

(58) Field of Classification Search
CPC ..... G01N 15/1031; A01F 12/181; A01F 7/06; A01D 41/1272; A01D 41/1243
See application file for complete search history.

(56) References Cited

U.S. PATENT DOCUMENTS

| | | | |
|---|---|---|---|
| 4,004,289 A | 1/1977 | Kirk | |
| 4,036,065 A * | 7/1977 | Strelioff | G01P 13/0073 73/647 |
| 4,951,031 A * | 8/1990 | Strubbe | A01D 41/1273 340/684 |
| 5,046,362 A | 9/1991 | Strubbe | |
| 5,939,888 A * | 8/1999 | Nelson | G01N 22/04 324/641 |
| 6,146,268 A | 11/2000 | Behnke et al. | |
| 7,584,663 B2 * | 9/2009 | Missotten | G01N 15/1031 460/45 |
| 7,877,969 B2 * | 2/2011 | Behnke | A01D 41/1277 701/50 |
| 10,188,036 B2 * | 1/2019 | Loukili | G06V 20/56 |
| 10,285,329 B2 | 5/2019 | Baumgarten et al. | |
| 2012/0004815 A1 * | 1/2012 | Behnke | A01D 41/1277 701/50 |
| 2013/0029734 A1 * | 1/2013 | Behnke | A01D 41/1276 460/101 |
| 2014/0135082 A1 * | 5/2014 | Batcheller | A01D 41/1275 460/5 |
| 2014/0208851 A1 * | 7/2014 | Bischoff | A01D 41/1273 73/593 |
| 2015/0080069 A1 * | 3/2015 | Fuchs | A01D 41/1272 460/1 |
| 2016/0003656 A1 * | 1/2016 | Gelinske | G01N 33/0098 73/861.18 |
| 2017/0094901 A1 * | 4/2017 | French, Jr. | A01F 12/444 |
| 2019/0059232 A1 * | 2/2019 | Ricketts | A01F 12/444 |
| 2019/0133037 A1 * | 5/2019 | Todd | G01N 33/025 |
| 2019/0137416 A1 | 5/2019 | Todd et al. | |
| 2020/0077583 A1 | 3/2020 | Vandike et al. | |
| 2020/0084966 A1 * | 3/2020 | Corban | A01D 61/02 |
| 2020/0134392 A1 * | 4/2020 | Gui | G06T 3/40 |
| 2021/0084816 A1 * | 3/2021 | Bussmann | A01F 12/58 |
| 2021/0105941 A1 * | 4/2021 | Yu | G01S 13/88 |
| 2022/0354054 A1 * | 11/2022 | Hermann | A01D 41/1243 |
| 2022/0354055 A1 * | 11/2022 | Hermann | A01D 61/008 |
| 2022/0408643 A1 * | 12/2022 | Somarowthu | G01S 7/412 |

FOREIGN PATENT DOCUMENTS

| | | | | |
|---|---|---|---|---|
| EP | 1832863 B1 | | 6/2016 | |
| EP | 3056076 B1 * | | 11/2017 | ......... A01D 41/1273 |
| WO | 2016040959 A1 | | 3/2016 | |
| WO | 2019040642 A1 | | 2/2019 | |

* cited by examiner

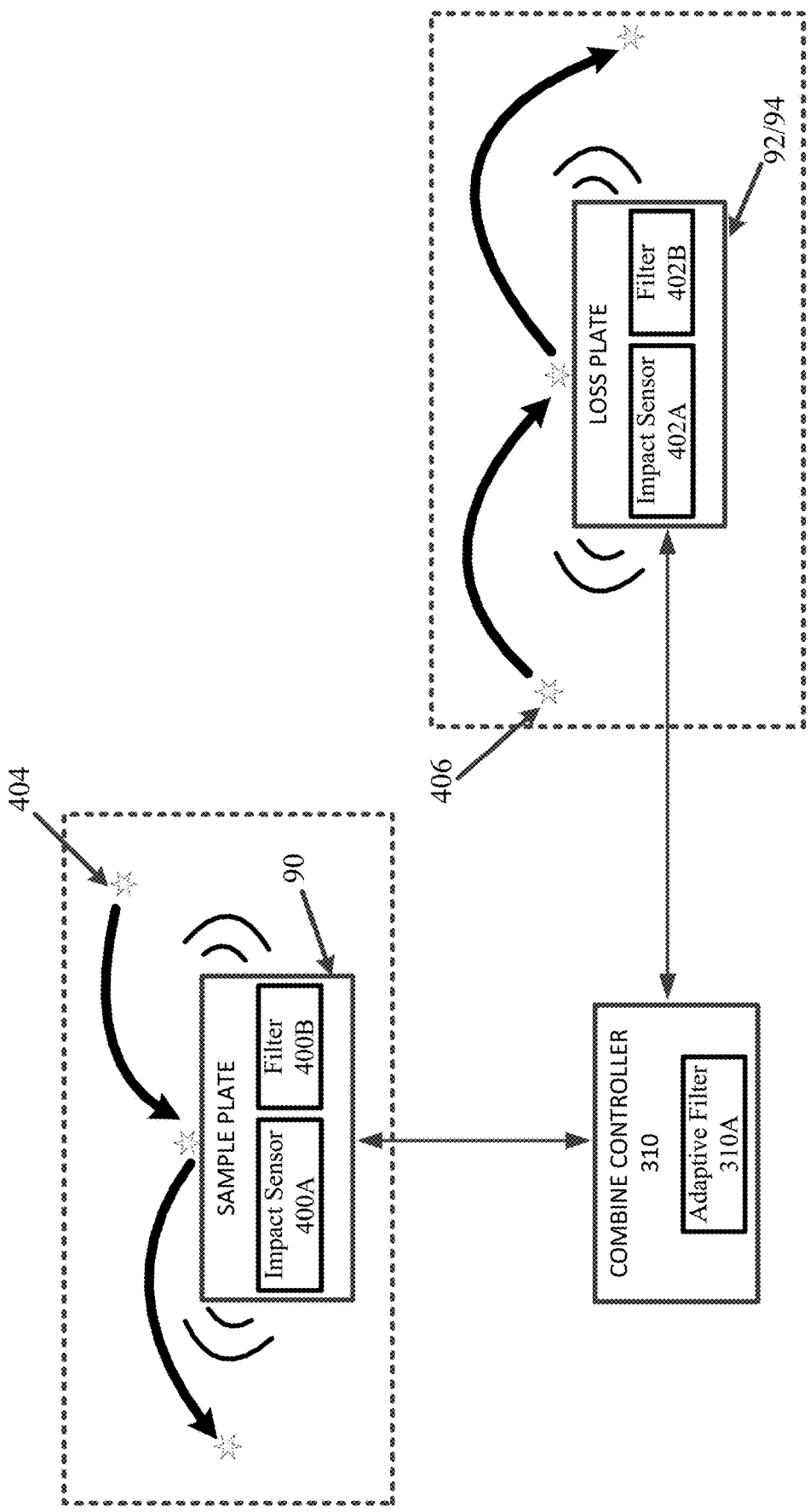

ACTIVE LOSS MONITOR FOR A HARVESTER

FIELD OF THE INVENTION

The invention relates to an active loss monitor system and method for implementation in an agricultural harvester combine.

BACKGROUND OF THE INVENTION

Conventional combines harvest crops by performing various operations including chopping the crop and collecting grain in a grain bin. These conventional combines are susceptible to grain loss.

SUMMARY OF THE INVENTION

An embodiment includes a combine having a feeder housing for receiving harvested crop, a separating system for threshing the harvested crop to separate grain from residue, a grain sample sensor for detecting frequencies of impacts of the separated grain on the grain sample sensor, a grain loss sensor for detecting frequencies of impacts of residue and lost grain on the grain loss sensor, and a controller that controls the combine. The controller is configured to receive, from the grain sample sensor, the frequencies of the impacts of the separated grain, receive, from the grain loss sensor, the frequencies of the impacts of the residue and the lost grain, set a detection frequency band based on the frequencies of the impacts of the separated grain, filter the frequencies of the impacts of the residue and the lost grain based on the detection frequency band, determine, from the filtered frequencies, grain loss information, and indicate the grain loss information to an operator of the combine, or control the combine based on the grain loss information.

Another embodiment includes a method for operating a combine including a feeder housing for receiving harvested crop, a separating system for threshing the harvested crop to separate grain from residue, a grain sample sensor for detecting frequencies of impacts of the separated grain on the grain sample sensor, a grain loss sensor for detecting frequencies of impacts of residue and lost grain on the grain loss sensor, and a controller that controls the combine. The method includes receiving, by the controller from the grain sample sensor, the frequencies of the impacts of the separated grain, receiving, by the controller from the grain loss sensor, the frequencies of the impacts of the residue and the lost grain, setting, by the controller, a detection frequency band based on the frequencies of the impacts of the separated grain, filtering, by the controller, the frequencies of the impacts of the residue and the lost grain based on the detection frequency band, determining, by the controller, from the filtered frequencies, grain loss information, and indicating, by the controller, the grain loss information to an operator of the combine, or control the combine based on the grain loss information.

BRIEF DESCRIPTION OF THE FIGURES

FIG. 4A is a view of the communication between the combine control system, the sample plate and the loss plate, according to an embodiment of the invention.

DETAILED DESCRIPTION OF THE INVENTION

Aspects of the disclosure provide methods and systems for determining grain loss based on frequency content of grain impacts. In various embodiments described throughout the specification, the system samples the frequency content of impacts for collected grain, and then adjusts the analysis of the frequency content of impacts for lost grain.

The terms "grain" and "residue" are used principally throughout this specification for convenience but it is to be understood that these terms are not intended to be limiting. "Grain" refers to that part of the crop material which is threshed and separated from the discardable part of the crop material, which is referred to as non-grain crop material, material other than grain (MOG). "Residue" refers to MOG that is to be discarded from the combine. Also the terms "fore", "aft", "left," and "right", when used in connection with the agricultural harvester (e.g. combine) and/or components thereof are usually determined with reference to the direction of forward operative travel of the combine, but again, they should not be construed as limiting.

Figure 1A:
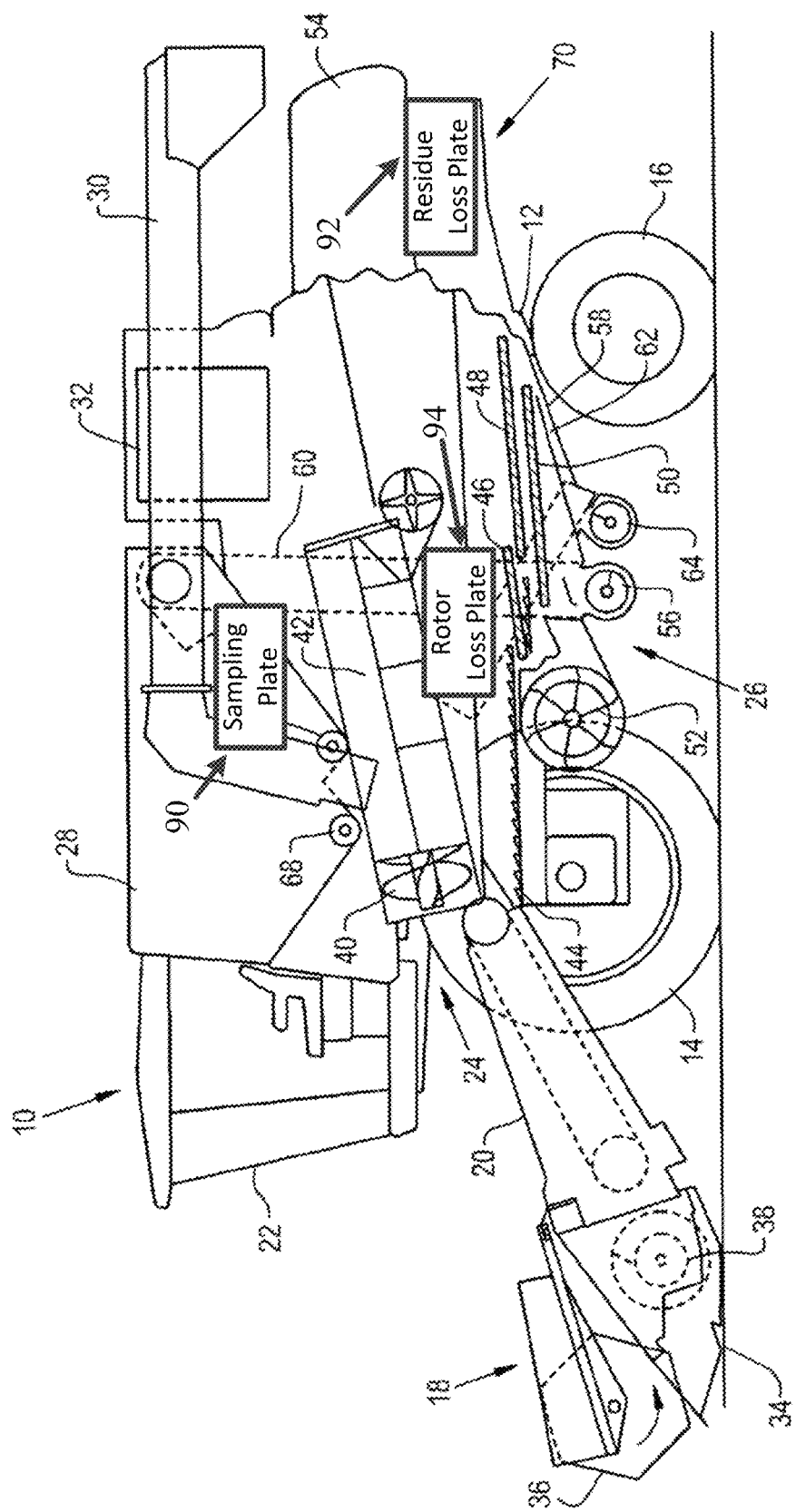
FIG. 1A is a side view of a combine, according to an embodiment of the invention.

Referring now to the drawings, and more particularly to FIG. 1A, there is shown one embodiment of an agricultural harvester in the form of a combine 10 (e.g. longitudinal rotary combine), which generally includes a chassis 12, ground engaging wheels 14 and 16, a header 18, a feeder housing 20, an operator cab 22, a threshing and separating system 24, a cleaning system 26, a grain tank 28, and an unloading auger 30.

Front wheels 14 are larger flotation type wheels, and rear wheels 16 are smaller steerable wheels. Motive force is selectively applied to front wheels 14 through a power plant in the form of a diesel engine 32 and a transmission (not shown). Although combine 10 is shown as including wheels, is also to be understood that combine 10 may include tracks, such as full tracks or half-tracks.

Header 18 is mounted to the front of combine 10 and includes a cutter bar 34 for severing crops from a field during forward motion of combine 10. A rotatable reel 36 feeds the crop into header 18, and a double auger 38 feeds the severed crop laterally inwardly from each side toward feeder housing 20. Feeder housing 20 conveys the cut crop to threshing and separating system 24, and is selectively vertically movable using appropriate actuators, such as hydraulic cylinders (not shown).

Threshing and separating system 24 generally includes a rotor 40 at least partially enclosed by and rotatable within a corresponding perforated concave 42. The cut crops are threshed and separated by the rotation of rotor 40 within concave 42, and larger MOG elements, such as stalks, leaves and the like are discharged from residue system 70 of combine 10. Smaller elements of crop material including grain and smaller MOG materials including particles lighter than grain, such as chaff, dust and straw, are discharged through perforations of concave 42. A grain loss sensor referred to as a rotor loss plate 94 may be positioned at or near the end of perforated cage 42. Rotor loss plate 94 may be a metal plate for detecting impacts of grain and MOG by way of sensing electronics enclosed therein. For example, rotor loss plate 94 may include an accelerometer for measuring vibrations caused by grain and MOG impacts. The frequencies the plate vibrations due to the impact can then be used to determine how much grain is hitting rotor loss plate 94 (e.g. this may be the rate of grain impacts or the total number of grain impacts). This determination can be quantified as rotor grain loss (e.g. grain that separating assembly 24 did not properly separate from the MOG). Based on the rotor loss information, the combine controller (not shown) can adjust parameters (e.g. rotor speed, concave 42 positioning, etc.) of separating assembly 24 in an attempt to reduce future rotor grain loss.

The combine controller may be a programmable logic controller, micro-controller, etc. The combine controller is programmable by the operator of the combine through a user (e.g. operator) interface, or through a remote computer. The operator, for example, enters commands through the user interface. In response to these commands, the controller sends control signals to the various actuators of combine 10.

Grain which has been separated by the threshing and separating assembly 24 falls onto a grain pan 44 and is conveyed toward cleaning system 26. Cleaning system 26 may include an optional pre-cleaning sieve 46, an upper sieve 48 (also known as a chaffer sieve), a lower sieve 50 (also known as a cleaning sieve), and a cleaning fan 52. Grain on sieves 46, 48 and 50 is subjected to a cleaning action by fan 52 which provides an airflow through the sieves to remove chaff and other impurities such as dust from the grain by making this material airborne for discharge from straw hood 54 of combine 10. Grain pan 44 and pre-cleaning sieve 46 oscillate in a fore-to-aft manner to transport the grain and finer non-grain crop material to the upper surface of upper sieve 48. Upper sieve 48 and lower sieve 50 are vertically arranged relative to each other, and likewise oscillate in a fore-to-aft manner to spread the grain across sieves 48, 50, while permitting the passage of cleaned grain by gravity through the openings of sieves 48, 50.

The remaining non-grain crop material (i.e. residue) proceeds through a residue handling system 70. Residue handling system 70 includes a chopper, a chopper pan, counter knives, a windrow door, a windrow chute and a residue spreader, which are not shown in FIG. 1A. When combine 10 is operating in the chopping and spreading mode, the chopper is set to a relatively high speed (e.g. 3,000 RPM), the counter knives may be engaged, the windrow door is closed and the residue spreader is running (e.g. rotating). This causes the non-grain crop material to be chopped in to pieces of approximately 6 inches or less and spread on the ground in a fairly uniform manner. In contrast, when combine 10 is operating in the windrow mode, the chopper is at a relatively low speed (e.g. 800 RPM), the counter knives are disengaged and the windrow door is open. The residue spreader may continue operation to spread only the chaff, with the crop material passing through the passageway created by the open windrow door and guided by a windrow chute as it exits the combine.

Similar to rotor loss sensor 94, another grain loss sensor referred to as a residue loss plate 92 may be positioned in residue system 70. Residue loss plate 92 may also include an accelerometer for measuring vibrations caused by grain and MOG impacts. The frequencies of these vibrations can then be used to determine how much grain being thrown by the chopper is hitting residue loss plate 92. This determination can be quantified as residue grain loss (e.g. grain that residue handling system 70 is ejecting from the combine). Based on the residue loss information, the combine controller (not shown) can adjust parameters (e.g. chopper speed/positioning, etc.) of residue handling system 70 in an attempt to reduce future residue grain loss.

The clean grain output by separating assembly 24 falls to a clean grain auger 56 positioned crosswise below and in front of lower sieve 50. Clean grain auger 56 receives clean grain from each sieve 48, 50 and from bottom pan 58 of cleaning system 26. Tailings from cleaning system 26 fall to a tailings auger trough 62. The tailings are transported via tailings auger 64 and return auger 66 to the upstream end of cleaning system 26 for repeated cleaning action. Clean grain auger 56 conveys the clean grain laterally to conveyor system including a generally vertically arranged grain elevator 60 for transport to grain tank 28.

Similar to loss sensors 92/94, another impact sensor referred to as sampling plate 90 may be positioned in grain tank 28. Sampling plate 90 may include an accelerometer for measuring vibrations caused by grain impacts as the clean grain is conveyed from grain elevator 60 into the grain tank. The frequencies of these vibrations can then be used to determine the impact frequencies of the grain hitting sampling plate 90. This determination can be quantified as clean grain frequency information (e.g. the vibrational frequency of the plate due to the impact of the grain free of any MOG). Based on the clean grain frequency information, the combine controller (not shown) can filter the frequencies of the vibrations determined by loss sensors 92/94 in order to specifically look for frequencies that coincide with grain impacts (not MOG impacts). This can be accomplished by band bass filtering the frequencies detected loss sensors 92/94, where the parameters of the band bass filter are set based on the clean grain frequency information. More details of this process is discussed below with reference to other figures.

Figure 1B:
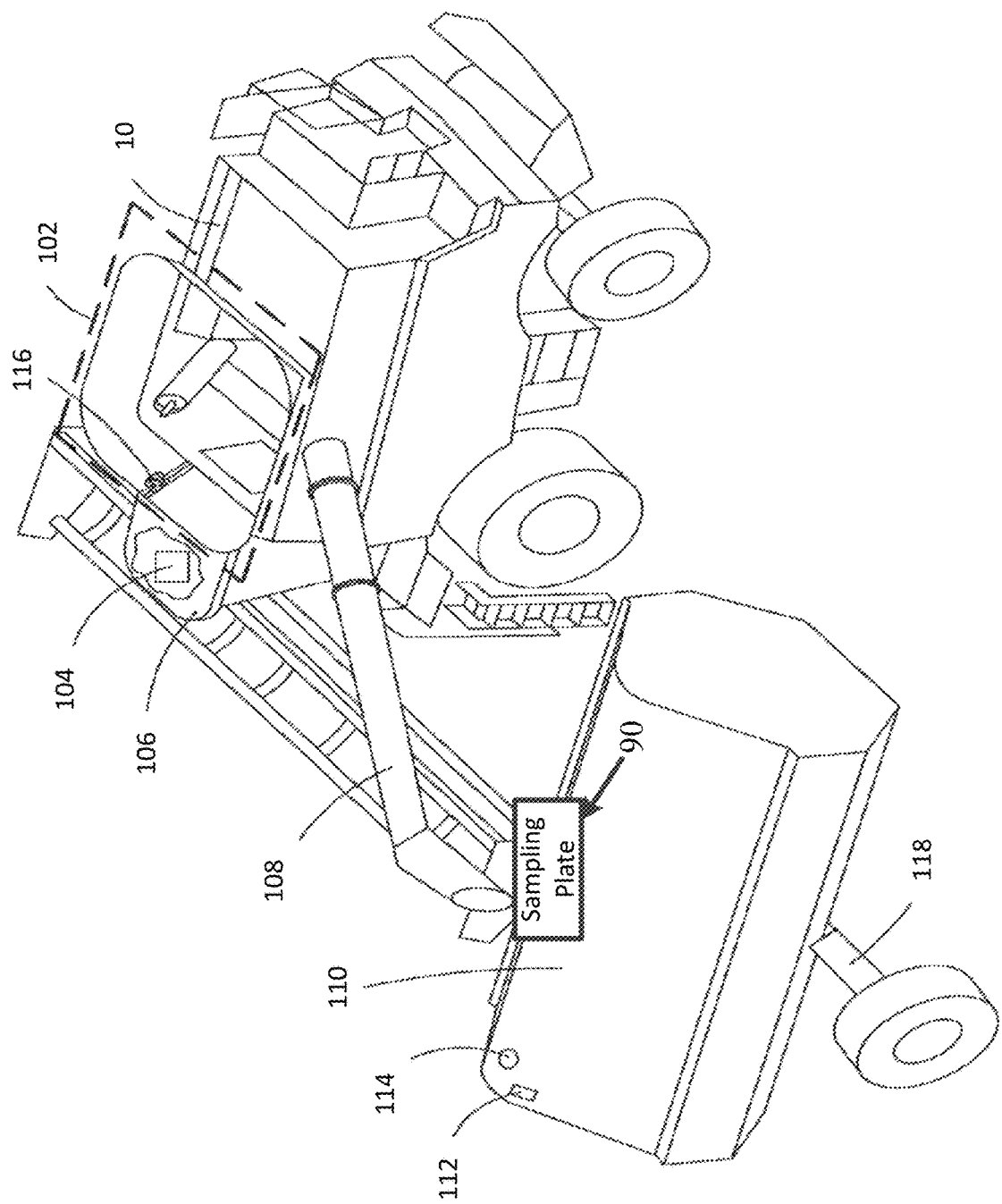
FIG. 1B is a perspective view of a combine, according to an embodiment of the invention.

A pair of grain tank augers 68 at the bottom of grain tank 28 convey the clean grain laterally within grain tank 28 to unloading auger 30 for discharge from combine 10. The clean grain sent to unloading auger 30 may be discharged from combine 10 to an adjacent grain cart 110 (see FIG. 1B) for storing the harvested grain. More specifically, as shown at FIG. 1B, combine 10 includes grain bin 102 for storing grain and unload tube 108 for carrying grain from grain bin 102 to grain cart 110 when a fill level sensor 112 detects that the grain has reached a certain level. Combine 10 includes a controller 104 in cab 106, and a transceiver (not shown). Grain cart 110 may also include a transceiver 114 for communicating with combine transceiver 116, bin level sensor 112 and a grain impact sensor such as sampling plate 90 (e.g. sampling plate 90 can be located in grain tank 28 or in grain cart 110. In some embodiments, exemplary controllers may be placed at different locations within the cab or other locations on the combine. In the example of FIG. 1B, the level of grain in grain bin 102 is detected by a bin level sensor 116, while the level of grain in grain cart 110 is detected by bin level sensor 112. The controller may control the combine to send grain from grain bin 102 to grain cart 110, and measure both levels to ensure that grain does not spill either from grain bin 102 or grain cart 110.

Figure 2A:
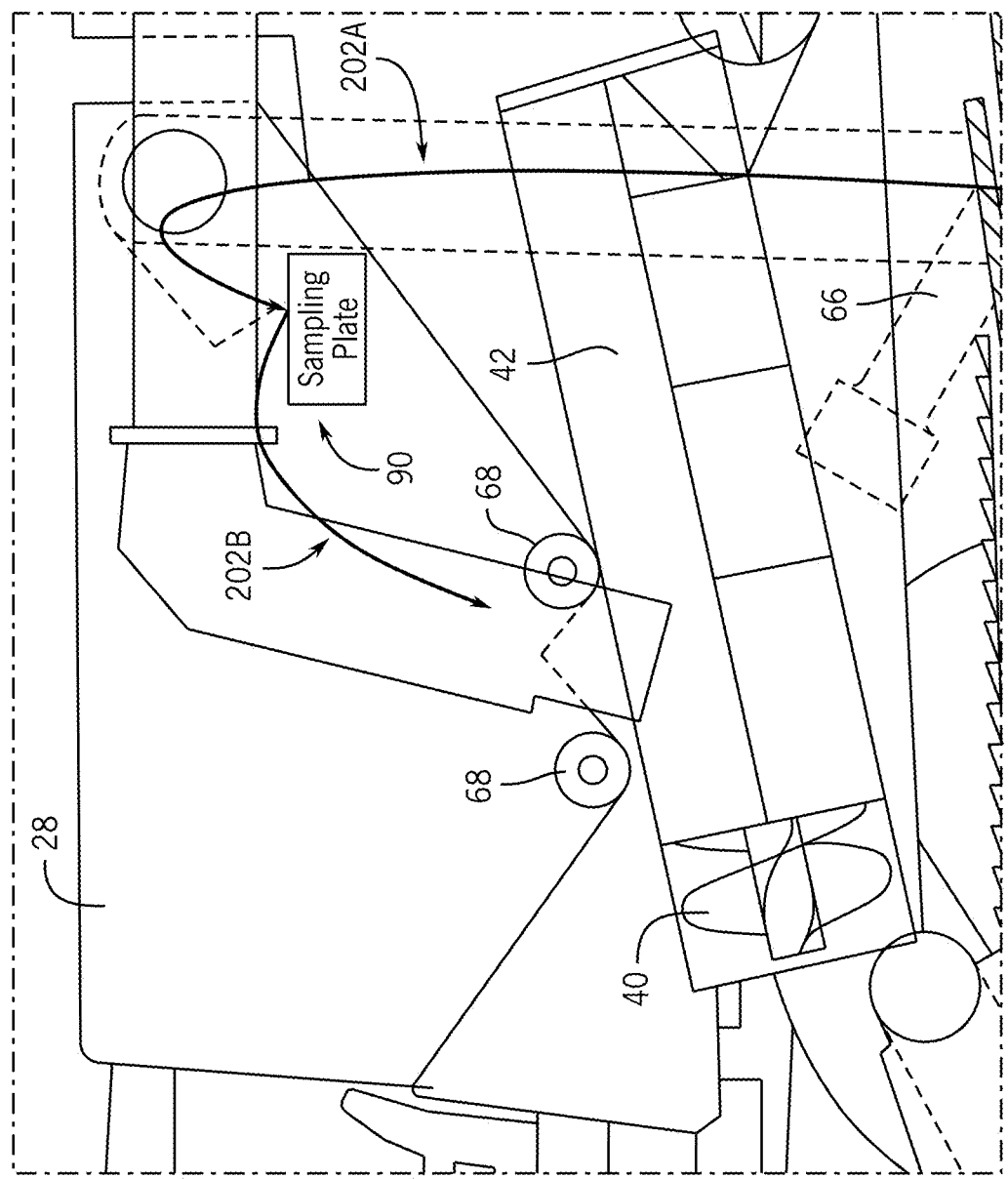
FIG. 2A is a section view of a combine grain collection system showing an example of grain collection flow, according to an embodiment of the disclosure.

FIG. 2A shows details of clean grain collection within grain tank 28. As described above, grain elevator 60 transports the clean grain vertically along path 202A. Upon reaching the top of the elevator, the clean grain falls onto sampling plate 90 and then falls into grain tank 28 along path 202B. Sampling plate 90 detects the frequencies of the clean grain impacts. This clean grain frequency information is then sent to the combine controller for processing (e.g. to determine band bass filter parameters for filtering the frequency information from loss plates 92/94).

Figure 2B:
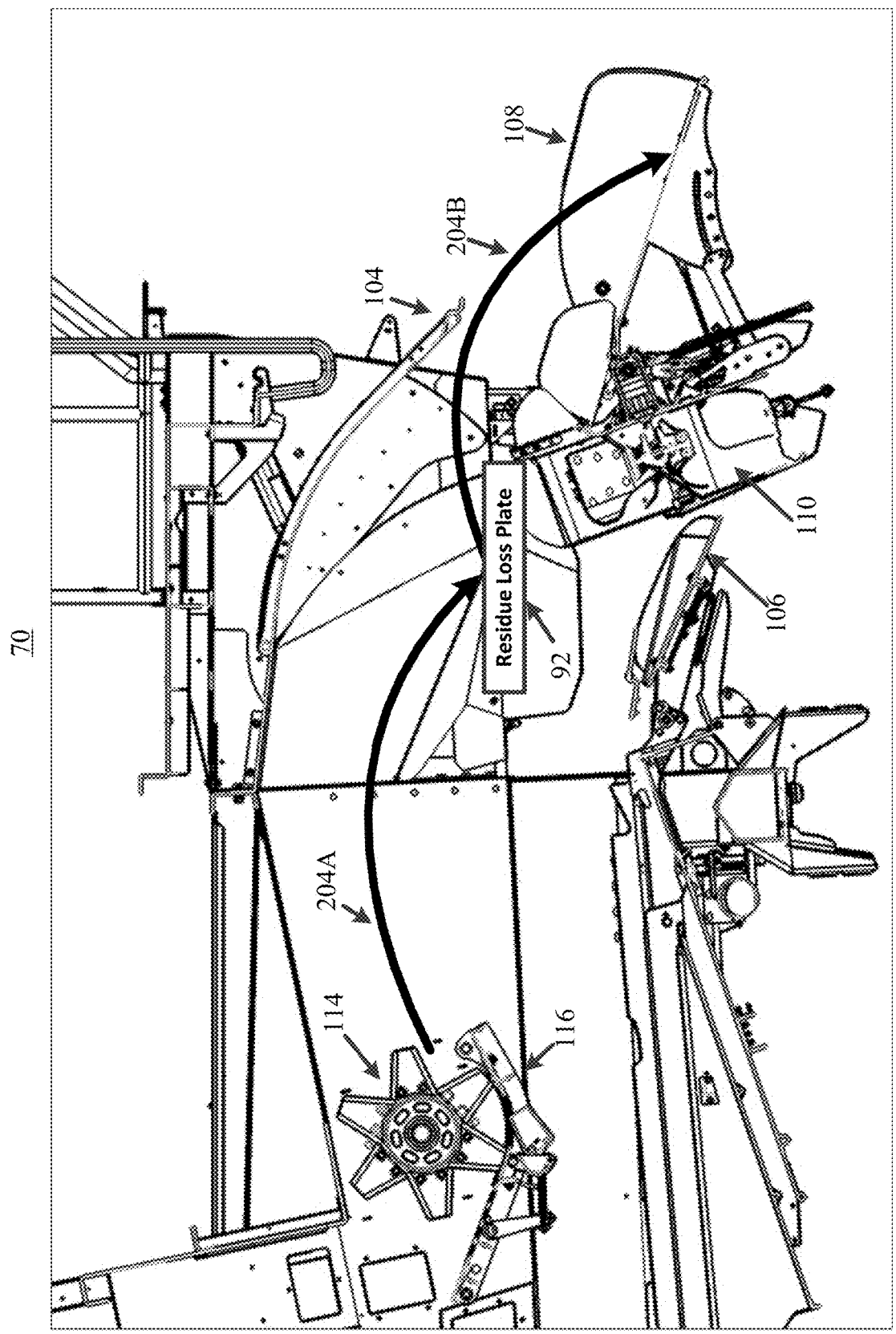
FIG. 2B is a section view of a combine residue system showing an example of residue flow, according to an embodiment of the disclosure.

FIG. 2B shows details of residue handling system 70. For example, as shown in FIG. 2B, residue handling system 70 includes windrow door 104, windrow chute 108, chaff pan 106, spreader impeller 110, spreader deflectors (not shown), chopper 114 and chopper pan 116. Although not shown in FIG. 2B, windrow door actuator, windrow chute actuator, spreader wheel system, spreader deflectors, and chopper 114 are electrically connected to combine controller 10. As described above, chopper 114 rotates and propels MOG (and any grain that was not properly separated from the MOG) towards the back of residue system 70 along path 204A. The MOG and grain then impacts residue loss plate 94 and is ejected from the combine via path 204B. Residue loss plate 94 detects the frequencies of the grain and MOG impacts and sends this residue loss frequency information to the combine controller for processing (e.g. determine residue system grain loss).

Figure 3:
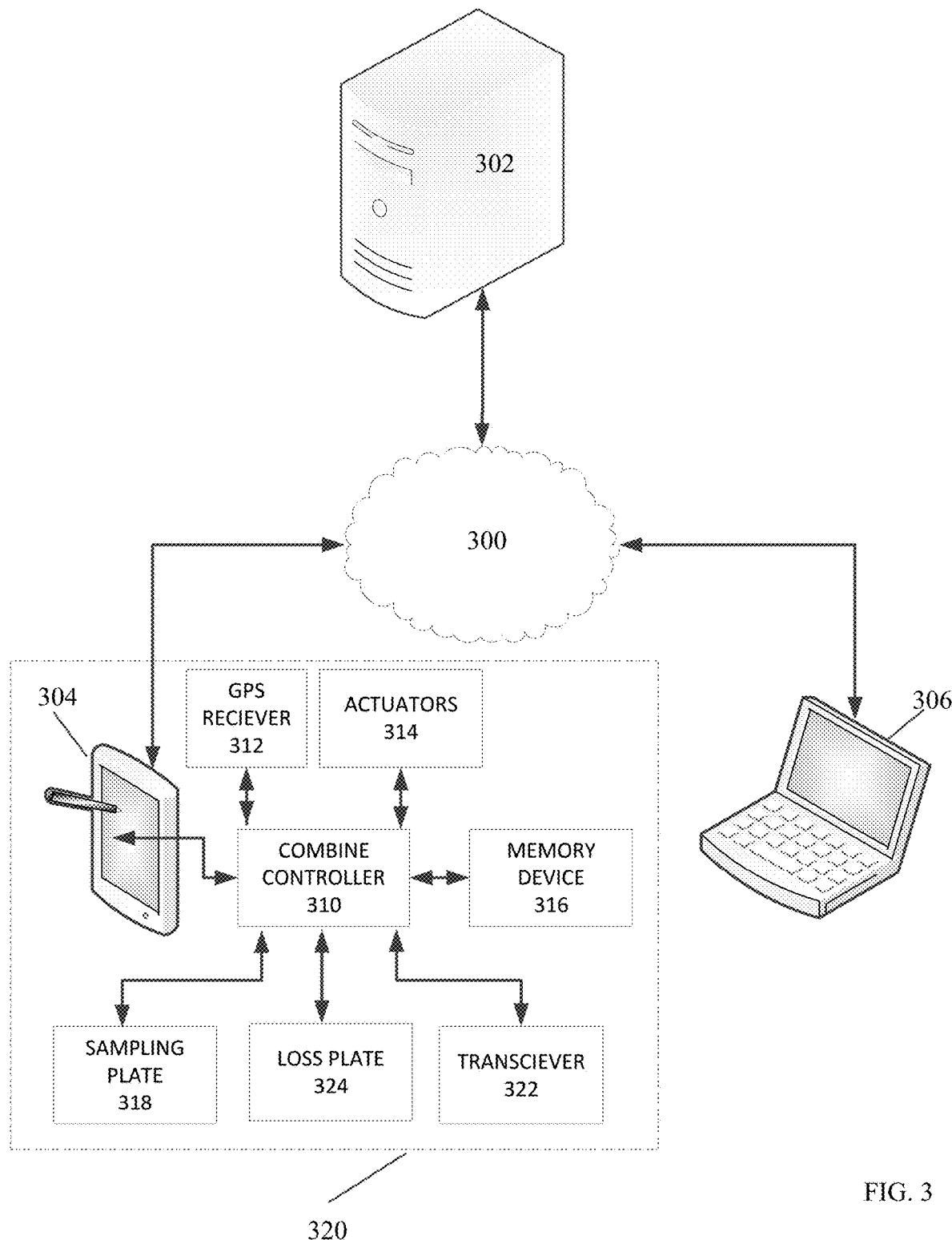
FIG. 3 is a view of the communication between the combine control system and an external network, according to an embodiment of the invention.

FIG. 3 shows an example of a system for controlling the combine. The system includes an interconnection between a control system 320 of combine 10, a remote PC 306 and a remote server 302 through network 300 (e.g. Internet). It should be noted that combine 10 does not have to be connected to other devices through a network. The controller of combine 10 can be a standalone system that receives operating instructions (e.g. grain loss alerts, etc.) through a user interface, or through a removable memory device (e.g. Flash Drive).

Prior to operating combine 10, an operator may designate grain information (e.g. type of grain, moisture content of grain, etc.) as well as grain loss alert levels. This grain information may also be determined by analyzing images of the grain captured by a camera (not shown). In one example, the operator uses interface 304 of the combine control system or PC 306 located at remote location 308. Interface 304 and PC 306 allow the operator to view locally stored parameters from memory device 316 and/or download parameters from server 302 through network 300. The operator may select (via Interface 304 or PC 306) appropriate grain loss alert levels based on various factors including, among others, the type of crop to be harvested by the combine, and the terrain. Once the grain loss alert levels are selected, the operator can begin harvesting. Combine controller 310 then controls actuators 314 (e.g. thresher, chopper, etc.) based on the instructions. For example, the loss plate 324 may be used during harvesting to compare the detected grain loss to alert levels set by the operator. When a specified grain loss level is reached, the alert output to the operator. Harvesting may also be tracked and aided by GPS receiver 312.

During harvesting, controller 310, in conjunction with sample plate 318 determines optimal grain impact frequency filtering parameters which are used to filter the frequency information from loss plates 324 to determine accurate grain loss information. A detailed example of this operation is now described with reference to FIG. 4A which shows the communication between the combine controller 310, sample plate 90 and loss plates 92/94.

In general sample plate 90 and loss plates 92/94 have a similar structure that includes an impact sensors 400A/402A and optional filters 400B/402B. Impact sensors 400A/402A may be any type of transducer that is able to determine impact frequency. For example, impact sensors 400A/402A may include an accelerometer mounted to the plate that detects physical vibrations of the plate, or a microphone mounted in proximity to the plate that detects sound caused by the physical vibrations of the plate. Optional filters 400B/402B may be band pass filters having a band that is set by the manufacturer to detect vibrations in a given range that coincides with known grain impact frequencies, while suppressing non-grain vibrations such as vibrations caused by the combine engine and other combine actuators. This band may be fairly large given the wide range of possible grains that are to be detected.

In order to accurately filter the frequency information output from sample plate 90 and loss plates 92/94, an adaptive filter 310A is employed. Although shown as being part of combine controller 310, it is noted that adaptive filter 310A may be separate from combine controller 310 (e.g. adaptive filter 310A may be an intermediary between combine controller 310 and impact plates 90/92/94. In either case, combine controller 310A is able to adjust parameters (e.g. center frequency of the pass band, cutoff frequencies, etc.) of adaptive filter 310A.

During operation, as clean grain 404 hits sample plate 90, impact sensor 400A detects and passes the impact frequencies to combine controller 310 for further processing. Also, during operation, as residue 406 (e.g. grain and/or MOG) hits loss plates 92/94, impact sensor 402A detects and passes the impact frequencies to combine controller 310A for further processing. Knowing that the impact frequencies of the clean grain can be used as a frequency signature, combine controller 310 uses the impact frequencies of the clean grain to adjust parameters of adaptive filter 310A. Combine controller 310 then uses adaptive filter 310A to filter the impact frequencies received from impact sensor 402A. This effectively passes the frequencies that coincide with the clean grain, while suppressing the unwanted frequencies of the MOG. The combine controller 310 is then able compute accurate grain loss data based on these filtered frequencies (e.g. grain hits are used, while MOG hits are ignored). This ensures that MOG hits are not accidentally counted as part of the grain loss analysis.

Figure 4B:
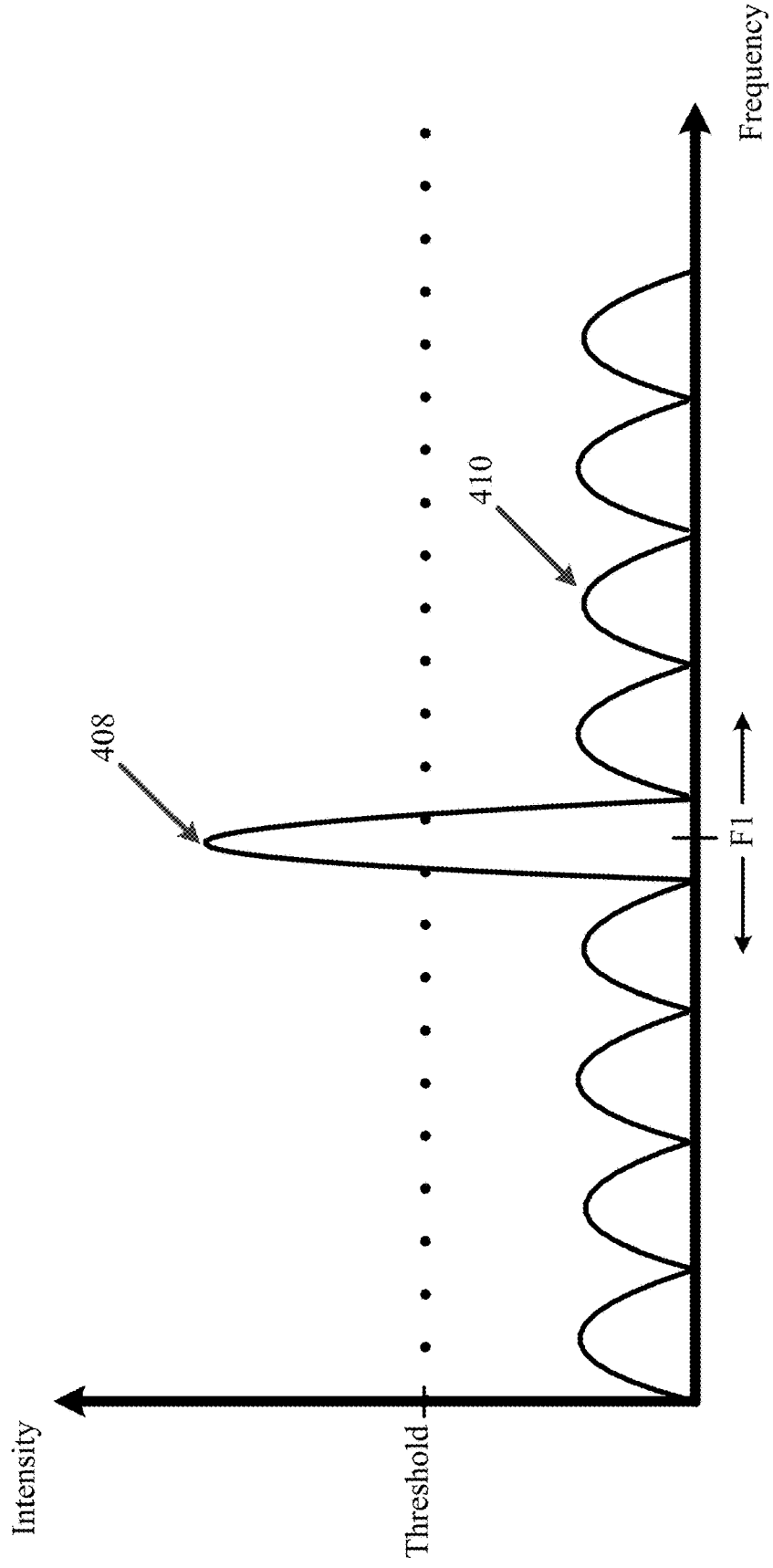
FIG. 4B is a data plot of frequency vs. intensity for grain hit detection, according to an embodiment of the invention.

An example frequency plot of a clean grain hit on sample plate 90 is shown in the data plot of FIG. 4B. In this example, a clean grain hit causes a large spike 408 in intensity at frequency F1 which is larger than an intensity threshold, while surrounding noise 410 is less than the intensity threshold due to the absence of MOG. The intensity threshold may be set by combine controller 310 in order to distinguish between hits and other vibrational noise. It is noted that F1 is not stationary and may vary due to various factors. These factors including but are not limited to type of grain and grain moisture level which both affect grain density, and therefore how hard or soft a piece of grain is when it hits plates 90/92/94. In general, as moisture content increases, impact frequency decreases and vice versa. Thus, hit frequency F1 can increase or decrease according to these factors.

Applicant's system accounts for these variations in F1 by periodically sampling the impact frequencies of the clean grain in order to adjust the parameters of the adaptive filter. For example, if impact frequencies of the clean grain decrease due to moisture, combine controller 310 adjusts the parameters of adaptive filter 310A to pass lower impact frequencies received from impact sensor 402A. This effectively passes the frequencies that coincide with the wet grain, while suppressing the frequencies of the MOG, thereby leading to more accurate loss data.

Figure 5:
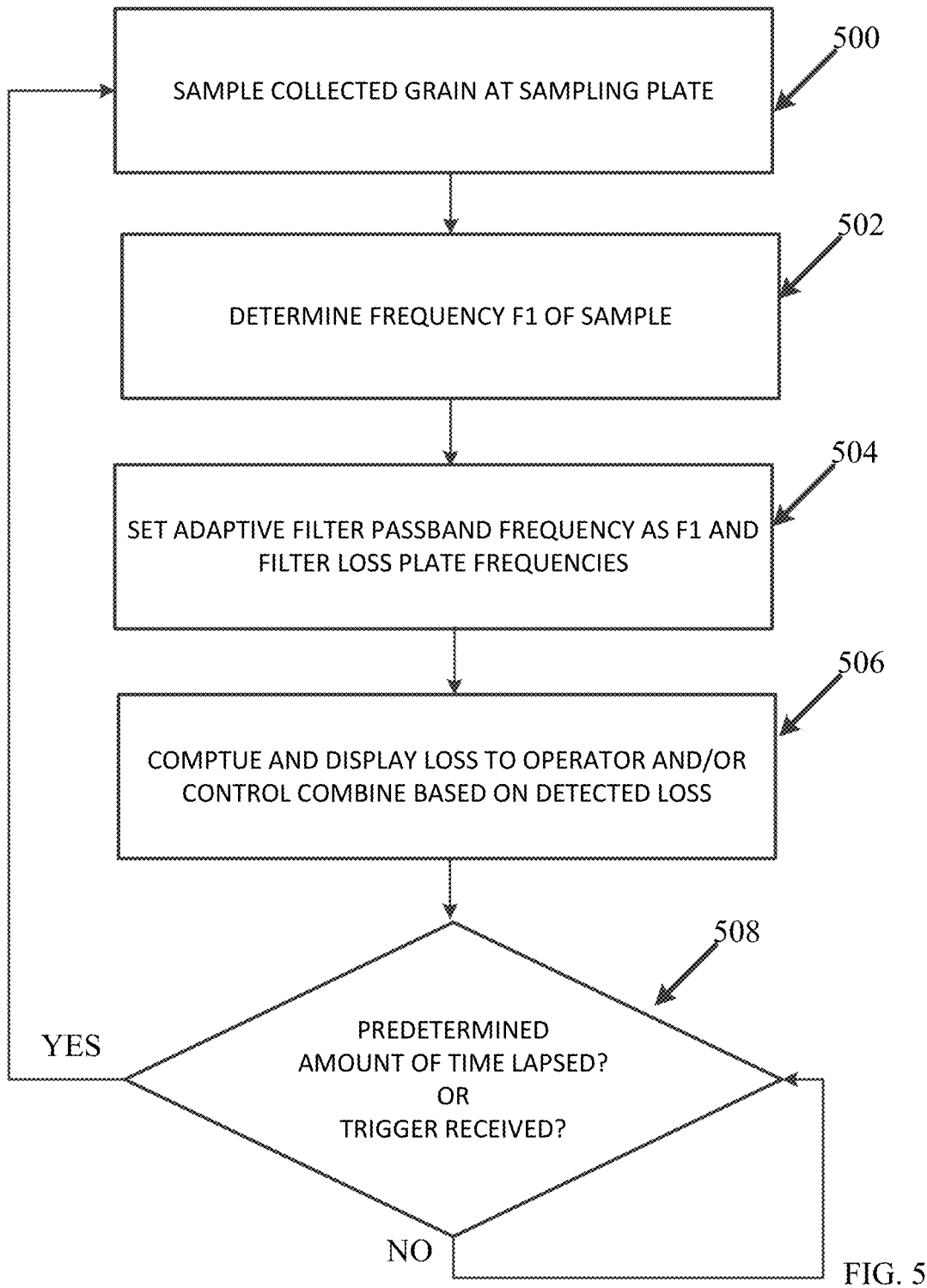
FIG. 5 is a flowchart for controlling the operational frequency of the loss plate, and controlling the combine based on the loss, according to an embodiment of the invention.

FIG. 5 is a flowchart for determining the frequency of the clean grain and then filtering the frequencies output by loss plates 92/94 to determine an accurate accounting of grain loss. In step 500, combine controller 310 controls sample plate 90 to sample the impact frequencies of clean grain. This sampling may occur over a given amount of time over numerous impacts to determine an accurate reading of impact frequencies of clean grain (e.g. the vibrational frequencies caused by impacts of clean grain). In step 502, combine controller 310 then determines a frequency signature (e.g. center frequency and bandwidth) based on the impact frequencies of clean grain (e.g. average center frequency, average bandwidth, etc.) on sample plate 90. A frequency band of a set range at a set center frequency may be set as the frequency signature to be used to adjusting the adaptive filter. In step 504, combine controller 310 then sets the parameters of the adaptive filter to pass this frequency signature. Combine controller 310 then compares the filtered frequencies detected by loss plates 92/94 to an intensity threshold to determine if a grain impact is detected or not. In step 506, combine controller 310 then computes grain loss (e.g. grain lost per unit time, percentage of grain lost to grain collected, total weight of grain lost, etc.) based on this information. In one example, combine controller 310 can display the grain loss to the combine operator. The combine operator may then manually adjust combine operational parameters (e.g. harvesting speed, rotor speed, etc.) in an attempt to reduce grain loss. In another example, combine controller 310 may use the grain loss to automatically adjust combine operational parameters (e.g. harvesting speed, rotor speed, etc.) in an attempt to automatically reduce grain loss. In step 508, combine controller 310 determines if and when the process should be repeated. This decision may be based on a predetermined time schedule (e.g. periodic sampling of clean grain) or based on a trigger. The trigger may be manually provided by the operator, or may be automatic based on varying conditions (e.g. increase/decrease in grain loss, terrain changes, moisture detections, weather conditions, etc.). These varying conditions may be detected by sensors such as moisture sensors, cameras or the like.

The steps of sampling grain, determining the frequency of the sampled grain, setting the filter frequency, computing the grain loss and controlling the combine based on the grain loss shown in steps 500-508 of FIG. 5 are performed by controller 310 upon loading and executing software code or instructions which are tangibly stored on a tangible computer readable medium 316, such as on a magnetic medium, e.g., a computer hard drive, an optical medium, e.g., an optical disc, solid-state memory, e.g., flash memory, or other storage media known in the art. Thus, any of the functionality performed by the controller 310 described herein, such as the steps shown in FIG. 5, are implemented in software code or instructions which are tangibly stored on a tangible computer readable medium. Upon loading and executing such software code or instructions by the controller 310, the controller 310 may perform any of the functionality of the controller 310 described herein, including the steps shown in FIG. 5 described herein.

It is to be understood that the operational steps are performed by the controller 310 upon loading and executing software code or instructions which are tangibly stored on a tangible computer readable medium, such as on a magnetic medium, e.g., a computer hard drive, an optical medium, e.g., an optical disc, solid-state memory, e.g., flash memory, or other storage media known in the art. Thus, any of the functionality performed by the controller 310 described herein is implemented in software code or instructions which are tangibly stored on a tangible computer readable medium. Upon loading and executing such software code or instructions by the controller 310, the controller 310 may perform any of the functionality of the controller 310 described herein, including any steps of the methods described herein.

The term "software code" or "code" used herein refers to any instructions or set of instructions that influence the operation of a computer or controller. They may exist in a computer-executable form, such as machine code, which is the set of instructions and data directly executed by a computer's central processing unit or by a controller, a human-understandable form, such as source code, which may be compiled in order to be executed by a computer's central processing unit or by a controller, or an intermediate form, such as object code, which is produced by a compiler. As used herein, the term "software code" or "code" also includes any human-understandable computer instructions or set of instructions, e.g., a script, that may be executed on the fly with the aid of an interpreter executed by a computer's central processing unit or by a controller.

Although the invention is illustrated and described herein with reference to specific embodiments, the invention is not intended to be limited to the details shown. Rather various modifications may be made in the details within the scope and range of equivalence of the claims and without departing from the invention.

The invention claimed is:

1. A combine comprising:
   a feeder housing for receiving harvested crop;
   a separating system for threshing the harvested crop to separate grain from residue;
   a grain sample sensor for detecting frequencies of impacts of the separated grain on the grain sample sensor;
   a grain loss sensor for detecting frequencies of impacts of residue and lost grain on the grain loss sensor; and
   a controller that controls the combine, the controller configured to:
   receive, from the grain sample sensor, the frequencies of the impacts of the separated grain,
   receive, from the grain loss sensor, the frequencies of the impacts of the residue and the lost grain,
   set a detection frequency band based on the frequencies of the impacts of the separated grain,
   filter the frequencies of the impacts of the residue and the lost grain based on the detection frequency band,
   determine, from the filtered frequencies, grain loss information, and
   indicate the grain loss information to an operator of the combine, or control the combine based on the grain loss information.

2. The combine of claim 1, further comprising:
   a residue system for processing the residue output from the separating system and ejecting the residue from the combine,
   wherein the grain loss sensor is located in the residue system to detect the frequencies of the impacts of the residue and the lost grain being ejected from the combine, and
   wherein the controller is further configured to receive, from the grain loss sensor, the frequencies of the impacts of the residue and the lost grain being ejected from the combine.

3. The combine of claim 2,
wherein the grain loss sensor is located between the separating system and the residue system to detect lost grain output from the separating system, and
wherein the controller is further configured to receive, from the grain loss sensor, the frequencies of the impacts of the residue and the lost grain being output by the separating system.

4. The combine of claim 1, further comprising:
a grain bin, the grain sample sensor being located in the grain bin; and
a conveyor system for conveying the separated grain into the grain bin;
wherein the controller is further configured to receive, from the grain sample sensor, frequencies of the impacts of the separated grain on the grain sample sensor as the grain is being conveyed into the grain bin.

5. The combine of claim 1,
wherein the controller is further configured to adjust the detection frequency band as the frequencies of the impacts of the separated grain change over time.

6. The combine of claim 1,
wherein the controller is further configured to trigger the grain sample sensor to detect the frequencies of the impacts of the separated grain.

7. The combine of claim 1,
wherein the controller is further configured to set the detection frequency band based on a moisture of the grain or a type of the grain.

8. The combine of claim 7,
wherein the controller is further configured to decreases a center frequency of the detection frequency band as the moisture of the grain increases, or as a density of the type of grain decreases.

9. The combine of claim 1,
wherein the controller is further configured to control the separating system based on the grain loss information to reduce future grain loss.

10. The combine of claim 9,
wherein the separating system includes a rotor enclosed in a cage for threshing the harvested crop, and
wherein the controller is further configured to control the separating system adjust speed of a rotor in the separating system based on the grain loss information, or adjust distance between the rotor and a cage in the separating system based on the grain loss information.

11. A method for operating a combine including a feeder housing for receiving harvested crop, a separating system for threshing the harvested crop to separate grain from residue, a grain sample sensor for detecting frequencies of impacts of the separated grain on the grain sample sensor, a grain loss sensor for detecting frequencies of impacts of residue and lost grain on the grain loss sensor, and a controller that controls the combine, the method comprising:
receiving, by the controller from the grain sample sensor, the frequencies of the impacts of the separated grain;
receiving, by the controller from the grain loss sensor, the frequencies of the impacts of the residue and the lost grain;
setting, by the controller, a detection frequency band based on the frequencies of the impacts of the separated grain;
filtering, by the controller, the frequencies of the impacts of the residue and the lost grain based on the detection frequency band;
determining, by the controller, from the filtered frequencies, grain loss information; and
indicating, by the controller, the grain loss information to an operator of the combine, or control the combine based on the grain loss information.

12. The method of claim 11, further comprising:
processing, by a residue system, the residue output from the separating system and ejecting the residue from the combine, the grain loss sensor being located in the residue system to detect the frequencies of the impacts of the residue and the lost grain being ejected from the combine; and
receiving, by the controller from the grain loss sensor, the frequencies of the impacts of the residue and the lost grain being ejected from the combine.

13. The method of claim 12,
receiving, by the controller from the grain loss sensor, the frequencies of the impacts of the residue and the lost grain being output by the separating system, the grain loss sensor being located between the separating system and the residue system to detect lost grain output from the separating system.

14. The method of claim 11, further comprising:
receiving, by the controller from the grain sample sensor, frequencies of the impacts of the separated grain on the grain sample sensor as the grain is being conveyed into a grain bin by a conveyor system, the grain sample sensor being located in the grain bin.

15. The method of claim 11,
adjusting, by the controller, the detection frequency band as the frequencies of the impacts of the separated grain change over time.

16. The method of claim 11,
triggering, by the controller, the grain sample sensor to detect the frequencies of the impacts of the separated grain.

17. The method of claim 11,
setting, by the controller, the detection frequency band based on a moisture of the grain or a type of the grain.

18. The method of claim 17,
decreasing, by the controller, a center frequency of the detection frequency band as the moisture of the grain increases, or as a density of the type of grain decreases.

19. The combine of claim 11,
controlling, by the controller, the separating system based on the grain loss information to reduce future grain loss.

20. The method of claim 19,
controlling, by the controller, the separating system to adjust speed of a rotor in the separating system based on the grain loss information, or adjust distance between the rotor and a cage in the separating system based on the grain loss information, the rotor being enclosed in the cage for threshing the harvested crop.

* * * * *